US012766176B2

(12) United States Patent
Zou et al.

(10) Patent No.: US 12,766,176 B2
(45) Date of Patent: Oct. 20, 2026

(54) DEBITTERING KUDINGCHA EXTRACT, PREPARATION METHOD AND FINGERPRINT DETECTION METHOD THEREOF

(71) Applicants: Chenland Nutritionals Inc., Irvine, CA (US); Qingdao Chenland Health Industry Group Co., Ltd., Qingdao (CN)

(72) Inventors: Shengcan Zou, Qingdao (CN); Xin Li, Qingdao (CN); Jie Wang, Qingdao (CN); Li Li, Qingdao (CN); Shanglong Wang, Qingdao (CN); Fang Fan, Qingdao (CN); Jinli Chen, Qingdao (CN)

(73) Assignees: Chenland Nutritionals Inc., Irvine, CA (US); Qingdao Chenland Health Industry Group Co., Ltd., Qingdao (CN)

( * ) Notice: Subject to any disclaimer, the term of this patent is extended or adjusted under 35 U.S.C. 154(b) by 663 days.

(21) Appl. No.: 18/109,287

(22) Filed: Feb. 14, 2023

(65) Prior Publication Data

US 2023/0263850 A1 Aug. 24, 2023

(30) Foreign Application Priority Data

Aug. 25, 2022 (CN) ......................... 202211027923.7
Dec. 1, 2022 (CN) ......................... 202211536244.2

(51) Int. Cl.
*A61K 36/185* (2006.01)
*B01J 20/26* (2006.01)
*G01N 30/34* (2006.01)

(52) U.S. Cl.
CPC ........... *A61K 36/185* (2013.01); *B01J 20/267* (2013.01); *G01N 30/34* (2013.01); *A61K 2236/19* (2013.01); *A61K 2236/331* (2013.01)

(58) Field of Classification Search
CPC .............. A61K 36/185; A61K 2236/19; A61K 2236/331; A61K 2236/00; A61K 2236/39; B01J 20/267; G01N 30/34; G01N 30/8686; G01N 2030/8813
See application file for complete search history.

(56) References Cited

U.S. PATENT DOCUMENTS

2010/0021615 A1 1/2010 Sato et al.
2011/0099688 A1 5/2011 Saleh
2016/0219897 A1 8/2016 Shimoda et al.

FOREIGN PATENT DOCUMENTS

CN 104311624 B * 4/2016 .......... C07J 71/0005
CN 112047988 A * 12/2020 ............. C07H 17/04
CN 115536542 A * 12/2022 ........... C07C 231/24

OTHER PUBLICATIONS

Fitzgerald, et al., "Enzymatic debittering of food protein hydrolysates" Biotechnology Advances, vol. 24, Issue 2, 2006, pp. 234-237. (Year: 2006).*
CN 104311624 B (PE2E English Machine Translation) (Year: 2016).*
CN 112047988 A (PE2E English Machine Translation) (Year: 2020).*
CN 115536542 A (PE2E English Machine Translation) (Year: 2022).*
Zhang, et al. "Optimization of Enzymolysis Extraction of Ursolic Acid from Ilex kudingcha C.J. Tseng and It's Protective Effects of CCI4-induced liver injury in mice" Science and Technology of Food Industry, vol. 40, No. 17, 2019. (English Translation of Abstract only) (Year: 2019).*

* cited by examiner

*Primary Examiner* — Susan Hoffman
(74) *Attorney, Agent, or Firm* — Hemisphere Law, PLLC

(57) ABSTRACT

A debittering Kudingcha extract, a preparation method and a fingerprint detection method thereof are disclosed, which relates to the technical field of extract preparation and detection. The extract is prepared from Kudingcha by enzymolysis, water extraction, concentration, drying, purification and enrichment by a macroporous resin column, and drying. When the macroporous resin column is arranged for purification and enrichment, it is first rinsed with pure water, and then eluted with an ethanol solution with volume fraction of 30-80%, and an ethanol eluent is collected. The Kudingcha extract is purified with macroporous resin, which can retain its effective ingredients to the greatest extent while reducing the bitter taste, and enhance the effect of improving energy and resisting fatigue. The quality control of products through fingerprint is conducive to the improvement of product stability and further promotion of products.

4 Claims, 11 Drawing Sheets

DEBITTERING KUDINGCHA EXTRACT, PREPARATION METHOD AND FINGERPRINT DETECTION METHOD THEREOF

CROSS REFERENCE TO RELATED APPLICATION

This patent application claims the benefit and priority of Chinese Patent Application No. 202211536244.2 filed on Dec. 1, 2022 and No. 202211027923.7 filed on Aug. 25, 2022, the disclosure of which are incorporated by reference herein in its entirety as part of the present application.

TECHNICAL FIELD

The present disclosure relates to the technical field of extract preparation and detection, and more specifically, to a debittering Kudingcha extract, a preparation method and a fingerprint detection method thereof.

BACKGROUND ART

Kudingcha is the dried leaf of the evergreen tree of *Ilex latifolia* Thunb. species in *Ilex* L. genus in *Ilex* L. family, which has the effects of clearing summer heat, detoxifying, producing fluids and so on.

There are more than 200 kinds of components in Kudingcha, such as Kudingsaponin, amino acid, vitamin C, polyphenols, flavonoids, caffeine, etc. Among them, phenolic acid, triterpene saponins and flavonoids are considered as the pharmaceutical active components in Kudingcha, while chlorogenic acid is the main source of bitter taste of Kudingcha.

However, even though Kudingcha contains more active ingredients beneficial to health, its popularization and application are limited due to its strong bitter taste and extremely low oral acceptance. At present, all kinds of mixed drinks on the market improve the taste by covering up the bitter taste, which does not fundamentally solve the bitter taste of Kudingcha. Therefore, how to improve the bitter taste of Kudingcha and retain its active ingredients is an important problem to solve the difficulties in its promotion.

SUMMARY

In view of the above, the present disclosure provides a debittering Kudingcha extract, a preparation method and fingerprint detection method thereof. The Kudingcha extract is prepared by the combination of enzymolysis and water extraction, which is beneficial to the dissolution of effective components. The Kudingcha extract is purified with macroporous resin, which can retain its effective ingredients to the greatest extent while reducing the bitter taste, and enhance the effect of improving energy and resisting fatigue. The quality control of products through fingerprint is conducive to the improvement of product stability and further promotion of products.

In order to achieve the above purpose, technical solutions of the present disclosure are specifically described as follows.

A debittering Kudingcha extract with anti-fatigue effect is prepared from Kudingcha by enzymolysis, water extraction, concentration, drying, purification and enrichment by a macroporous resin column, and drying. The macroporous resin is crosslinked polystyrene adsorption resin. When the macroporous resin column is arranged for purification and enrichment, it is first rinsed with pure water, and then eluted with an ethanol solution with volume fraction of 30-80%, and an ethanol eluent is collected.

A preparation method of the debittering Kudingcha extract with anti-fatigue effect includes the following steps:

(1) crushing Kudingcha, adding water and an enzyme preparation, and carrying out enzymolysis;
(2) adding water after the enzymolysis, carrying out water extraction to obtain extraction solutions, then combining the extraction solutions, and carrying out filtering, concentrating and drying to obtain extract powder;
(3) preparing the extract powder into a solution by adding water, and then carrying out purification and enrichment with macroporous resin column:

loading sample, rinsing the macroporous resin column with pure water, discarding the water eluent, and carrying out elution with an ethanol solution with volume fraction of 30-80%, and collecting the ethanol eluent;

wherein the macroporous resin is crosslinked polystyrene adsorption resin; and (4) drying the ethanol eluent to obtain the debittering Kudingcha extract.

Preferably, in step (1), the mass ratio of Kudingcha to water is 1:2-1:3;

the enzyme preparation is a composite enzyme preparation compounded by cellulase, pectinase and plant hydrolysis composite enzyme in a mass ratio of 2:1:1;

the enzymolysis is carried out under following conditions: the amount of the enzyme preparation is 0.2%-0.3% of the dry sample of Kudingcha, the time of the enzymolysis is 40-60 min, the temperature is 45-50 °C, and the pH value is 4.5-5.5.

Preferably, in step (2), the mass ratio of the Kudingcha to water is 1:6-1:12;

the number of times of the extraction are 1-3, and each time is 1-3 h;

the filtering is carried out using an 80-100 mesh sieve; and the specific gravity of the concentrated extract obtained by the concentrating is 1.01-1.08.

Further preferably, in step (2), the mass ratio of the Kudingcha to water is 1:10; the number of times of the extraction are 2, and each time is 2 h, the filtering is carried out using a 60 mesh sieve; and the specific gravity of the concentrated extract obtained by the concentrating is 1.04-1.05.

Preferably, in step (3), the sample loading concentration is 3-10 mg/mL, and the sample loading volume is 1-3 times of the column volume;

the volume of pure water rinsing is 3-5 times of the column volume;

the elution volume of the ethanol solution is 2-4 times of the column volume; and the flow rate of the sample loading, pure water rinsing and ethanol solution elution is 1.5 times of column volume/h.

Further preferably, in step (3), the loading concentration is 3-6 mg/mL, and the loading volume is one time of the column volume; the volume of pure water rinsing is 3 times of the column volume; the elution volume of the ethanol solution is 3 times of the column volume.

Further preferably, in step (3), the volume fraction of ethanol solution is 40-80%.

Preferably, in step (3), the ratio of column height to diameter of the macroporous resin column is 1:6-1:8; and the crosslinked polystyrene adsorption resin is AB-8.

In step (1) or (4), the drying is spray drying or hypobaric drying;

the spray drying parameters are: inlet air temperature 120 °C, outlet air temperature 90 °C, centrifugal frequency 300 Hz, feed pump 17 rpm, induced air frequency 50 Hz.

A fingerprint detection method of the above debittering Kudingcha extract with anti-fatigue effect is provided, and the chromatogram is constructed by high performance liquid chromatography under the following chromatographic conditions:

the chromatographic column is octadecyl silane bonded silica gel chromatographic column;

the column temperature is 25-35 °C;

the flow rate is 0.9-1.1 mL/min;

the detection wavelength is 317-337 nm;

the mobile phase A is acetonitrile, the mobile phase B is 0.4% phosphoric acid water, and the gradient elution procedure is as follows:

| Time/min | Mobile phase A/% | Mobile phase B/% |
|---|---|---|
| 0.00~15.00 | 13→13 | 87→87 |
| 15.00~50.10 | 13→46 | 87→54 |
| 50.10~60.10 | 46→95 | 54→5 |
| 60.10~70.10 | 95→95 | 5→5 |
| 70.10~80.10 | 13→13 | 87→87 |

Preferably, the chromatographic column is C18, and the specification is 4.6×250 mm, 5 μm; the column temperature is 35 °C; the flow rate 1.0 mL/min; and the detection wavelength is 327 nm.

Preferably, the preparation method of test sample includes:

preparing Kudingcha extract into a solution by a methanol aqueous solution with a volume fraction of 50%, sealing and sonicating the solution for 30-60 min, shaking the sonicated solution well, and filtering the shaken solution to obtain a test sample solution for high performance liquid chromatography detection.

Preferably, the preparation method of 0.1 mg/mL reference substance includes:

weighing 10 mg of chlorogenic acid reference substance accurately, dissolving the chlorogenic acid reference substance in 100 mL of 50% methanol aqueous solution, filtering and shaking the same well.

The above detection methods shall be used to control the quality of products containing the debittering Kudingcha extract.

A preparation for improving energy and resisting fatigue is provided, which includes the above debittering Kudingcha extract and other acceptable excipients or additives.

Further, the dosage form of the preparation includes powder, granule, tablet, capsule, soft capsule, soft candy, oral liquid and any other acceptable dosage forms.

Compared with the prior art, the disclosure provides a debittering Kudingcha extract and a preparation method thereof. The preparation method is suitable for industrialization, and the prepared Kudingcha extract has good water solubility (1 g of the extract can be dissolved in 1-10 ml of water), low bitterness, good taste and good anti-fatigue activity. It has wide application and popularization prospect. In addition, it can be detected by a fingerprint detection method, which is beneficial to controlling product quality.

BRIEF DESCRIPTION OF THE DRAWINGS

In order to explain the embodiments of the present disclosure or the technical solutions in the prior art more clearly, the following drawings that need to be used in the description of the embodiments or the prior art are briefly introduced. Obviously, the drawings in the following description are only embodiments of the present disclosure. For those of ordinary skill in the art, other drawings can be obtained based on the drawings disclosed without creative work.

DETAILED DESCRIPTION OF THE EMBODIMENTS

Figure 1:
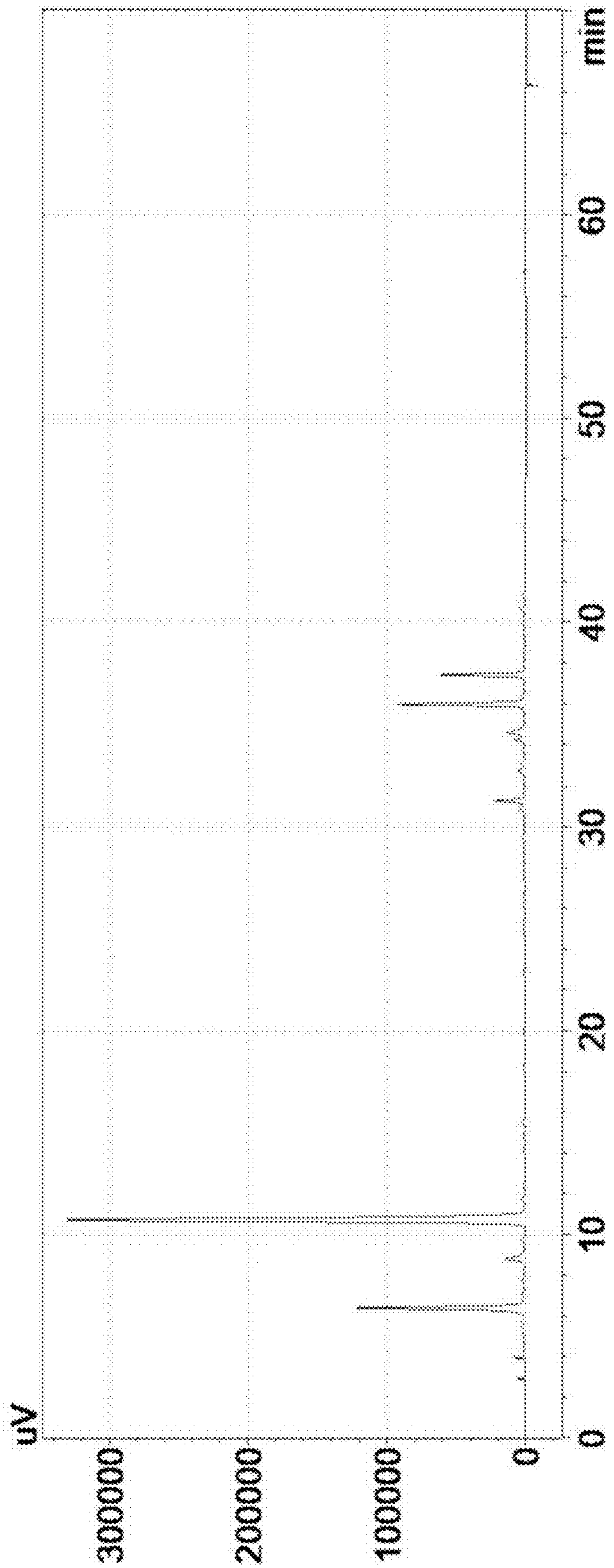
FIG. 1 shows a fingerprint of the Kudingcha extract A prepared in embodiment 1 (under the condition of mobile phase elution gradient 1)
Figure 2:
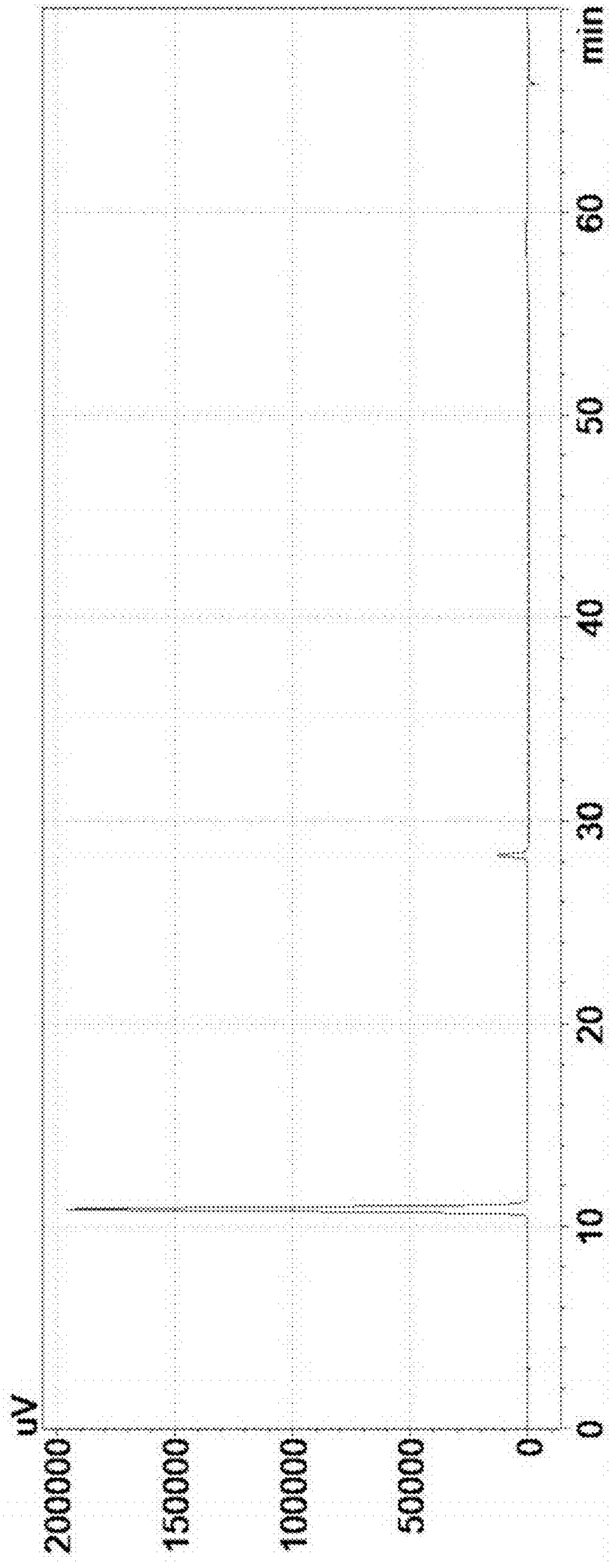
FIG. 2 shows a fingerprint of the chlorogenic acid standard (under the condition of mobile phase elution gradient 1)
Figure 3:
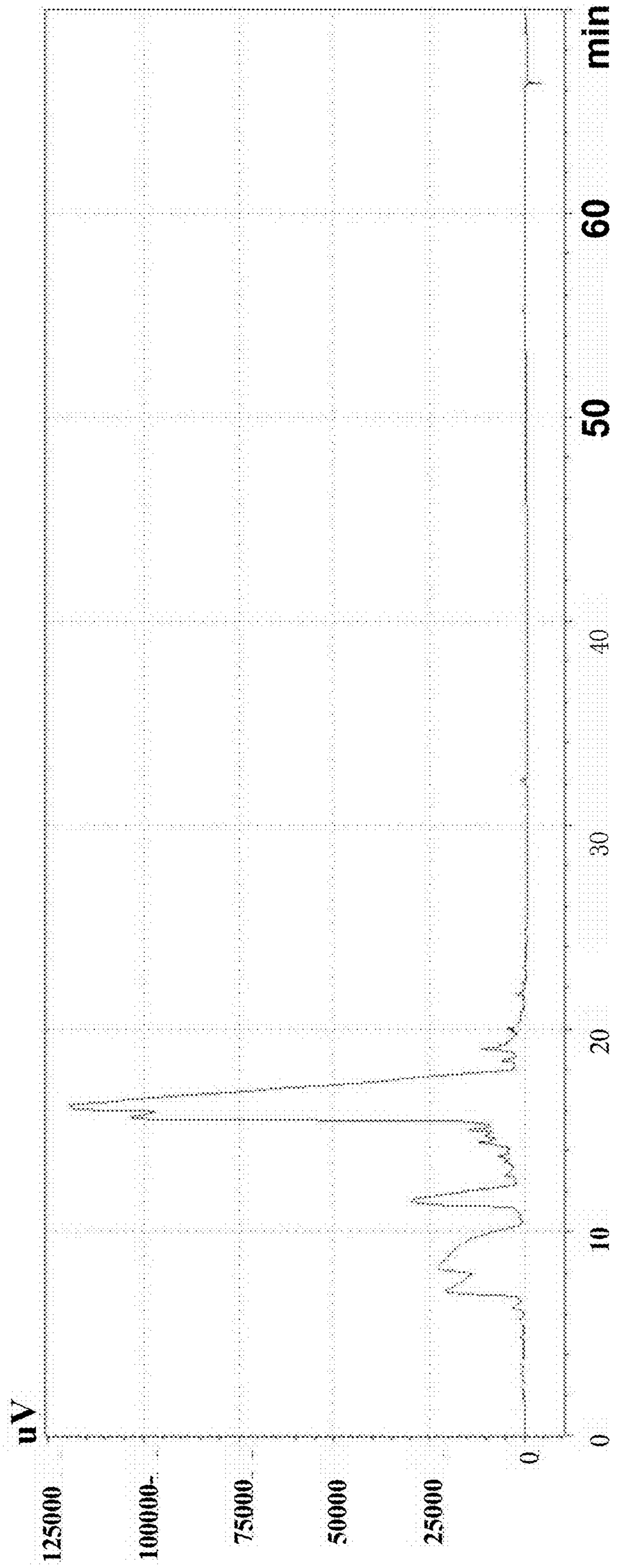
FIG. 3 shows a fingerprint of the Kudingcha extract A prepared in embodiment 1 (under the condition of mobile phase elution gradient 2)
Figure 4:
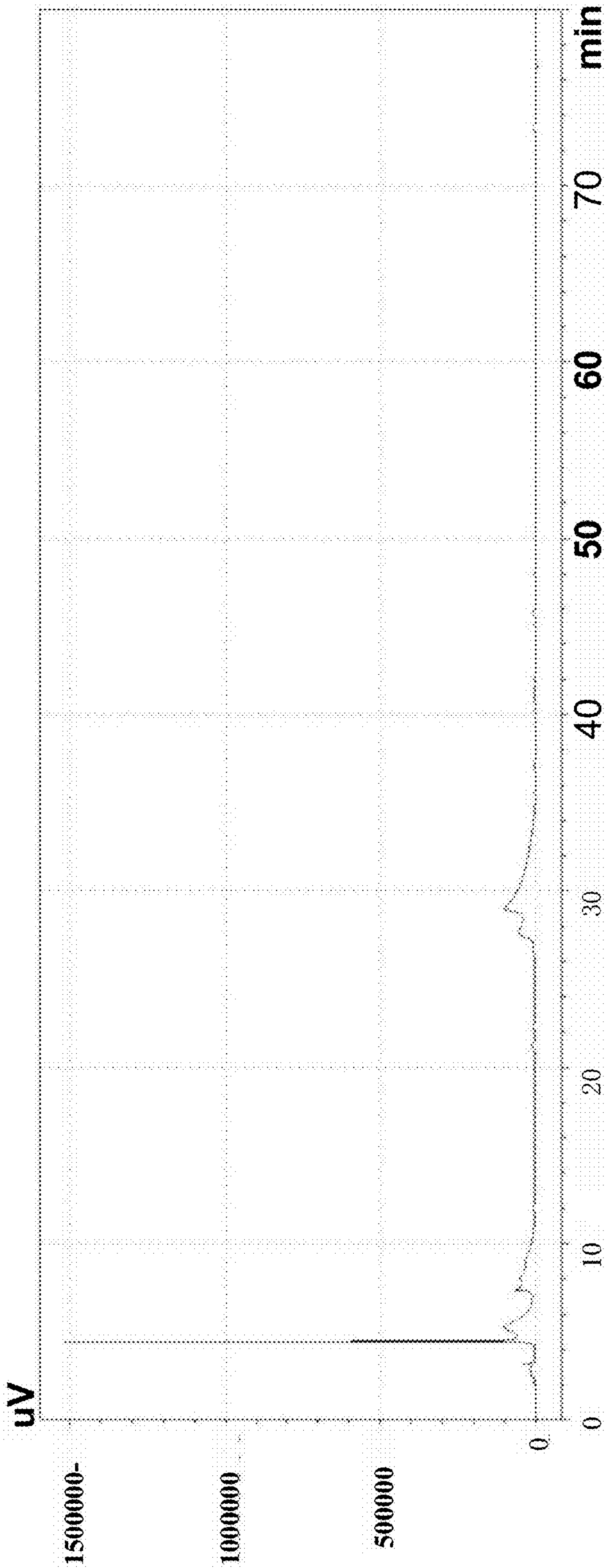
FIG. 4 shows a fingerprint of the Kudingcha extract A prepared in embodiment 1 (under the condition of mobile phase elution gradient 3)
Figure 5:
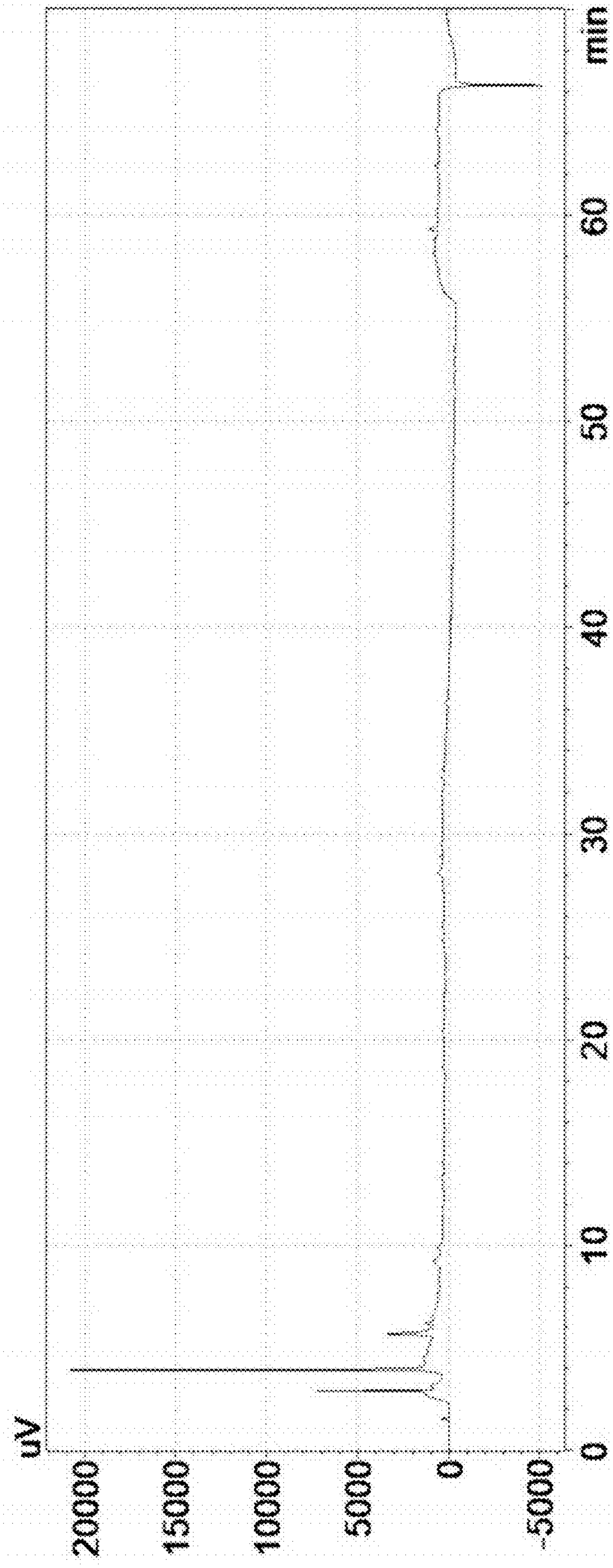
FIG. 5 shows a fingerprint of AB-8-1 Kudingcha extract prepared in embodiment 1.
Figure 6:
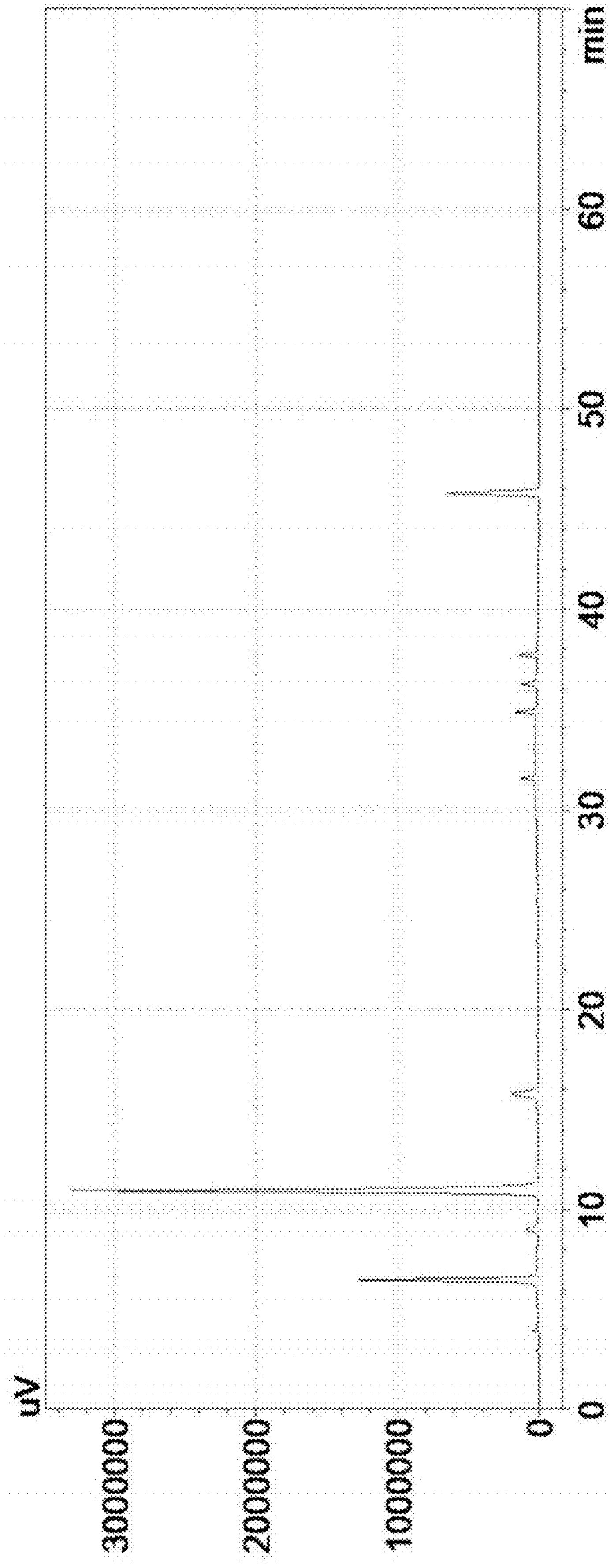
FIG. 6 shows a fingerprint of AB-8-2 Kudingcha extract prepared in embodiment 1.
Figure 7:
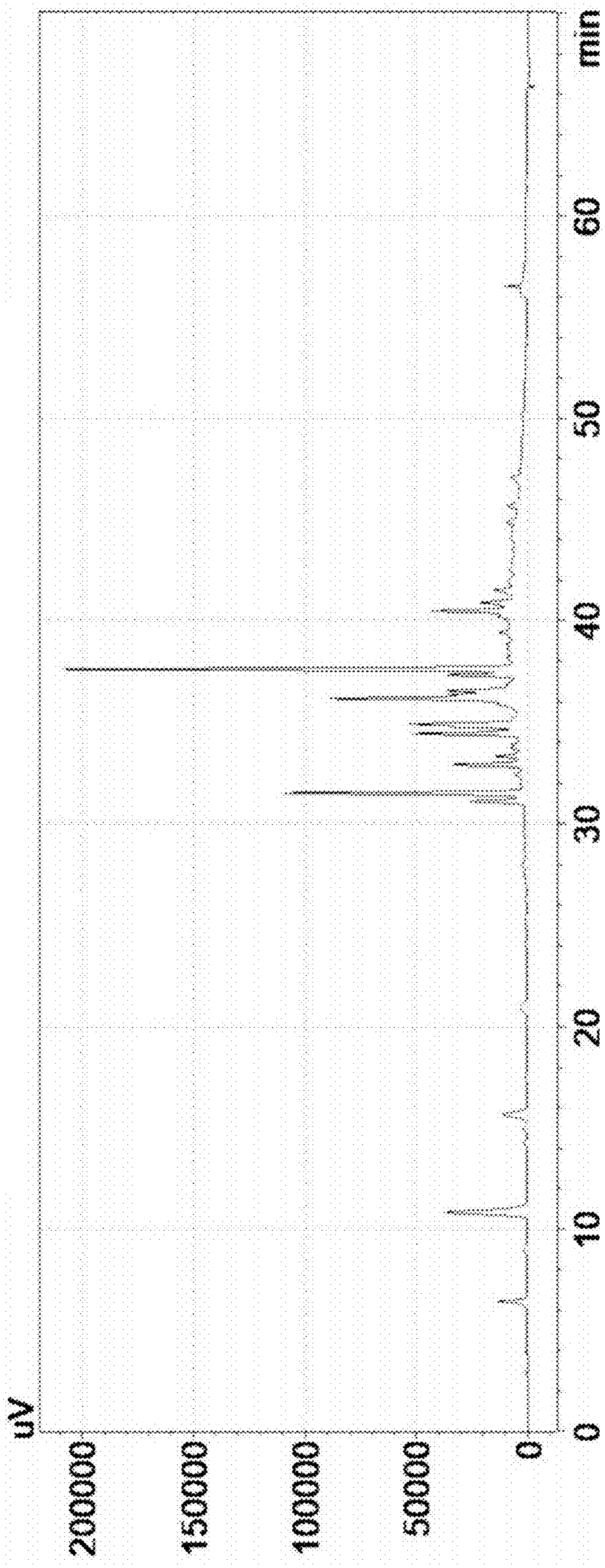
FIG. 7 shows a fingerprint of AB-8-3 Kudingcha extract prepared in embodiment 1.
Figure 8:
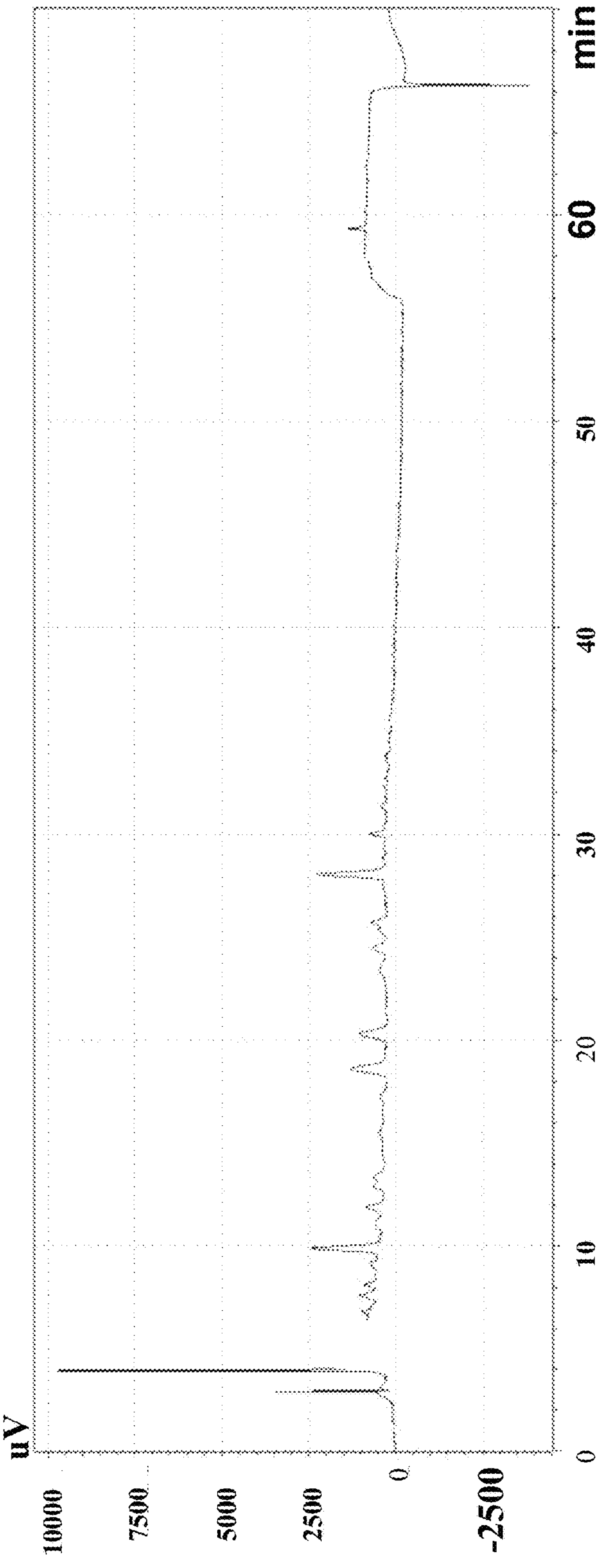
FIG. 8 shows a fingerprint of D101-1 Kudingcha extract prepared in comparative example 1.
Figure 9:
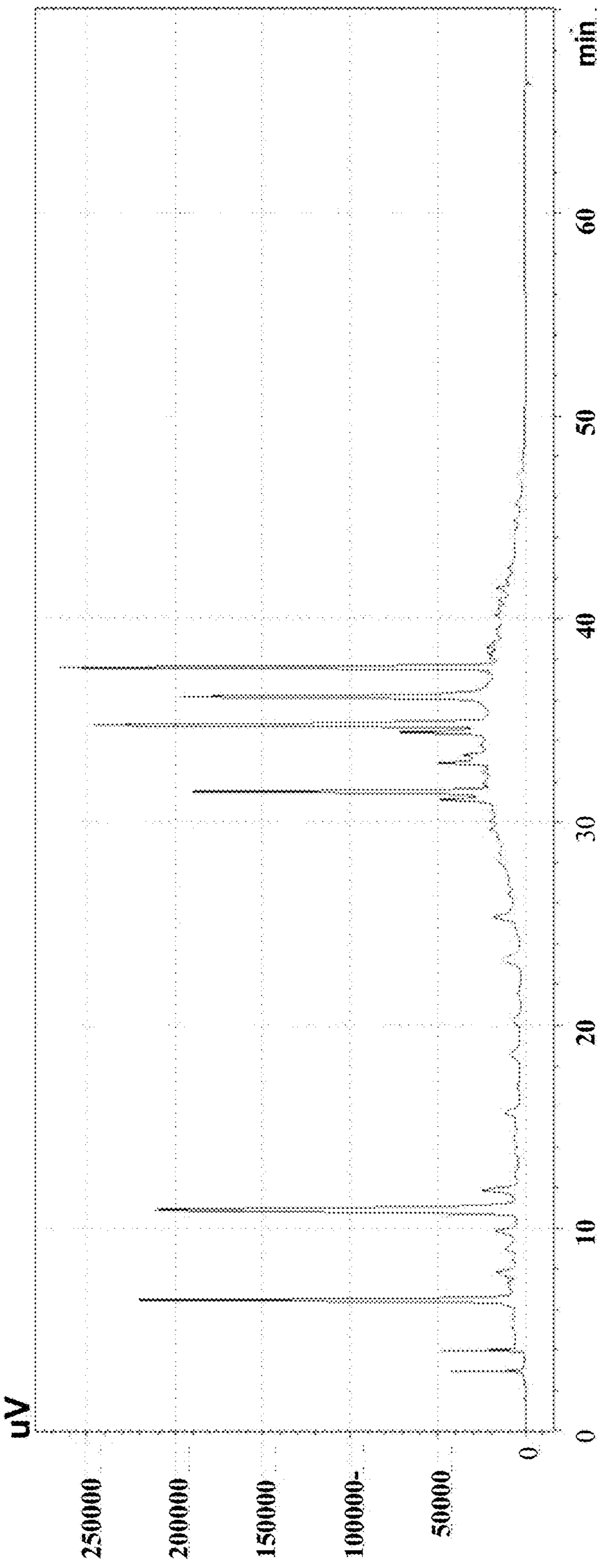
FIG. 9 shows a fingerprint of D101-2 Kudingcha extract prepared in comparative example 1.
Figure 10:
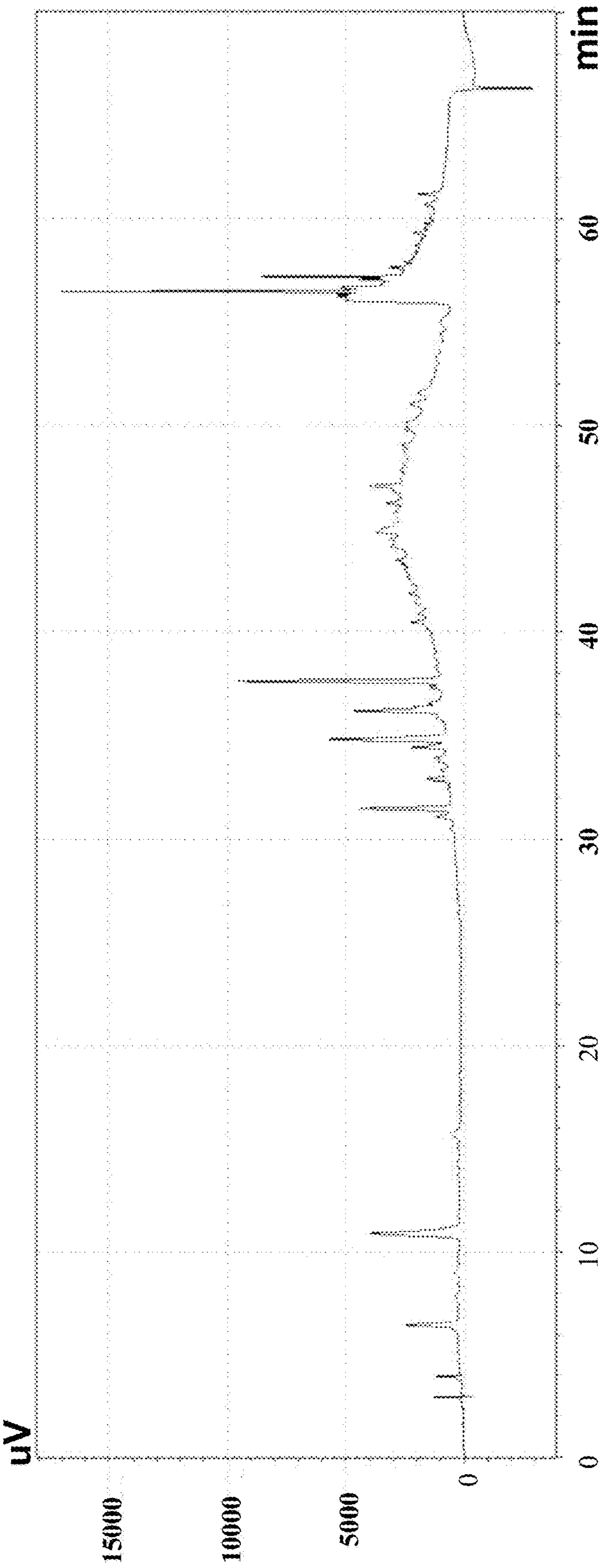
FIG. 10 shows a fingerprint of D101-3 Kudingcha extract prepared in comparative example 1.

Technical solutions of the present disclosure will be clearly and completely described below with reference to the embodiments. Obviously, the described embodiments are only part of the embodiments of the present disclosure, not all of them. Based on the embodiments of the disclosure, all other embodiments made by those skilled in the art without sparing any creative effort should fall within the protection scope of the disclosure.

For the special word "embodiment" here, any embodiment described as "exemplary" need not be interpreted as superior to or better than other embodiments. Unless otherwise specified, the performance index test in the embodiments of the application adopts the conventional test method in the field. It should be understood that the terms described in the application are only used to describe special embodiments, not to limit the contents disclosed in the application.

Unless otherwise specified, the technical and scientific terms used herein have the same meanings as those commonly understood by ordinary technicians in the technical field to which the application belongs. Other test methods and technical means not specifically noted in the application refer to those commonly used by ordinary technicians in the field.

Embodiment 1

Preparation of Sample 1: Kudingcha Extract 100 g of Kudingcha (dry leaves) was taken, crushed and sieved through 80 meshes, then 3 times of water was added. The enzymolysis temperature was set at 50 °C, and the pH of the material solution was adjusted to 5.0. The compound enzyme preparation was added for 40 min of enzymolysis, and the amount of added enzyme preparation was 0.2% of the amount of dry Kudingcha sample. After enzymolysis, water was added until 10 times of water for the first water extraction, then 8 times of water was added for the second extraction (the two times of extraction were atmospheric heating reflux extraction, the heating temperature was 100 °C, the condensation reflux temperature is 4 °C), and each water extraction lasted for 2 h. The extracts were combined, filtered through a 100-mesh sieve, and concentrated to a specific gravity of 1.04-1.05. Then centrifugal spray drying was carried out, wherein the parameters were: inlet air temperature 120 °C, outlet air temperature 90 °C, centrifugal frequency 300 Hz, feed pump 17 rpm, and induced air frequency 50 Hz. Then Kudingcha extract A was obtained, about 10 g, with a yield of about 10.55%.

0.84 g of the Kudingcha extract A was taken and diluted to 3 mg/mL solution with water. The activated AB-8 macroporous resin (soaked in ethanol for 24 h) was selected. The column with a diameter of 3.8 cm was taken, filled with a diameter-to-height ratio of 1:6, a filling height of 22.8 cm, and a filling volume of 258 $cm^3$, and rinsed with pure water until no ethanol smell.

The sample loading concentration was 3 mg/mL, and the sample loading volume was 1 time of the column volume 258 mL (the flow rate of sample loading, subsequent pure water rinsing and ethanol solution was 1.5 times of the column volume/h, that is, 2 drops/s). The rinsing with pure water was carried out for 3 times the column volume. After loading the sample, elution with pure water was carried out to obtain 258 mL of original solution (discard). The water rinsing solution was 3 times the column volume of 774 mL to obtain the water eluent AB-8-1 eluent. The elution was carried out with an ethanol solution with volume fraction of 40%, and the elution volume was twice the column volume to obtain 40% ethanol eluent AB-8-2 eluent. Then the elution was carried out with an ethanol solution with volume fraction of 80%, and the elution volume was twice the column volume to obtain 80% ethanol eluent AB-8-3 eluent. The AB-8-2 eluent and AB-8-3 eluent were evaporated to dryness to obtain 0.17 g of AB-8-2 Kudingcha extract and 0.14 g of AB-8-3 Kudingcha extract.

Embodiment 2

Preparation of Sample 2: Amplification Preparation of Kudingcha Extract 1 kg of Kudingcha (dry leaves) was taken, crushed and sieved through 80 meshes, then 3 times of water was added. The enzymolysis temperature was set at 50 °C, and the pH of the material solution was adjusted to 5.0. The compound enzyme preparation was added for 40 min of enzymolysis, and the amount of added enzyme preparation was 0.2% of the amount of dry Kudingcha sample. After enzymolysis, water was added until 10 times of water for the first water extraction, then 8 times of water was added for the second extraction (for two times of extraction, 10 times and 8 times of water was added respectively; the two times of extraction were atmospheric heating reflux extraction, the heating temperature was 100 °C, the condensation reflux temperature is 4 °C), and each water extraction lasted for 2 h. The extracts were combined, filtered through a 100-mesh sieve, and concentrated to a specific gravity of 1.04-1.05. Then centrifugal spray drying was carried out, wherein the parameters were: inlet air temperature 120 °C, outlet air temperature 90 °C, centrifugal frequency 300 Hz, feed pump 17 rpm, and induced air frequency 50 Hz. Then Kudingcha extract B was obtained, with a yield of about 10.00%.

28.26 g of the Kudingcha extract B was taken and diluted to 6 mg/mL solution with water. The activated AB-8 macroporous resin (soaked in ethanol for 24 h) was selected. The column with a diameter of 10 cm was taken, filled with a diameter-to-height ratio of 1:6, a filling height of 60 cm, and a filling volume of 4700 $cm^3$, and rinsed with pure water until no ethanol smell. The sample loading concentration was 6 mg/mL, and the sample loading volume is 1 time of the column volume 4700 mL (the flow rate of sample loading and subsequent pure water rinsing and ethanol solution elution was 1.5 times the column volume/h, that is, 2 drops/s). The rinsing with pure water was carried out for 3 times of the column volume. After loading the sample, elution with pure water was carried out to obtain 4700 mL of original solution (discard) and water rinsing solution 3 times the column volume of 14000 mL (discard). The elution was carried out with an ethanol solution with volume fraction of 40%, and the elution volume was twice the column volume to obtain 40% ethanol eluent. Then the 40% ethanol eluents were combined, concentrated, hypobaric dried, crushed and passed through 60 mesh sieve to obtain about 6 g of AB-8-4 Kudingcha extract, with a yield of about 21.23%.

In order to further prove the beneficial effects of the disclosure and better understand the disclosure, the product quality and performance of Kudingcha extract of the disclosure are further clarified through the following comparative examples and experiments, but it cannot be understood as the limitation of the disclosure. The product properties obtained from other determination experiments conducted by technicians in the art according to the above contents of the disclosure and the applications based on the above properties are also considered to fall within the protection scope of the disclosure.

Comparative Example 1

AB-8 macroporous resin was replaced with D101 macroporous resin, and the rest were the same as embodiment 1.

The water rinsing solution was 3 times the column volume of 774 mL to obtain the water eluent D101-1 eluent. The elution was carried out with an ethanol solution with volume fraction of 40%, and the elution volume was twice the column volume to obtain 40% ethanol eluent D101-2 eluent. Then the elution was carried out with an ethanol solution with volume fraction of 80%, and the elution volume was twice the column volume to obtain 80% ethanol eluent D101-3 eluent.

The D101-2 eluent and D101-3 eluent were evaporated to dryness to obtain 0.20 g of D101-2 Kudingcha extract and 0.18 g of D101-3 Kudingcha extract.

Experiment 1 Fingerprint

1. Instruments and Equipment

High performance liquid chromatograph: Shimadzu LC-20A;

Electronic balance: one-100000th analytical balance (Mettler Toledo MS105DU).

2. Reagents and Materials

Methanol (Fisher Chemical™, chromatographically pure), acetonitrile (Fisher Chemical™, chromatographically pure), water (Watsons™, distilled water); Microporous filter membrane (BOJIN, nylon 0.22 μm), syringe (Jiangxi Qingshantang medical device, 1 mL).

3. Chromatographic Conditions

Shimadzu InertSustain AQ-C18 (4.6×250 mm, 5 μm) with octadecyl silane bonded silica gel as filler; acetonitrile was used as mobile phase A, and phosphoric acid aqueous solution with volume fraction of 0.4% was used as mobile phase B, and gradient elution was performed according to Table 1-3; and the detection wavelength was 327 nm.

TABLE 1

| Mobile phase elution gradient 1 | | |
|---|---|---|
| Time (min) | Mobile phase A (%) | Mobile phase B (%) |
| 0.00~15.00 | 13→13 | 87→87 |
| 15.00~50.10 | 13→46 | 87→54 |
| 50.10~60.10 | 46→95 | 54→5 |
| 60.10~70.10 | 95→95 | 5→5 |
| 70.10~80.10 | 13→13 | 87→87 |

TABLE 2

| Mobile phase elution gradient 2 | | |
|---|---|---|
| Time (min) | Mobile phase A (%) | Mobile phase B (%) |
| 0.00~50.00 | 5→95 | 95→5 |
| 50.00~60.00 | 95→95 | 5→5 |
| 60.00~60.10 | 95→5 | 5→95 |
| 60.10~70.10 | 5→5 | 95→95 |

TABLE 3

| Mobile phase elution gradient 3 | | |
|---|---|---|
| Time (min) | Mobile phase A (%) | Mobile phase B (%) |
| 0.00~40.00 | 5→20 | 95→80 |
| 40.00~50.00 | 20→30 | 80→70 |
| 50.00~60.00 | 30→70 | 70→30 |
| 60.00~65.00 | 70→95 | 30→5 |
| 65.00~70.00 | 95→95 | 5→5 |
| 70.00~71.00 | 95→5 | 5→95 |
| 71.00~81.00 | 5→5 | 95→95 |

4. Sample Preparation 0.1 g of the Kudingcha extract A prepared in embodiment 1 was weighed accurately into a 100 mL conical flask, 25 mL of methanol aqueous solution with mass fraction of 50% was added to obtain a solution. And the solution was sonicated at 35 °C for 60 min and cooled to room temperature. Then the solution that has been made up of the weight loss was filtered and shaken well to obtain the test sample solution.

10 mg of chlorogenic acid reference substance was weighed accurately, dissolved in 100 mL of 50% methanol aqueous solution, filtered and shaken well to obtain the reference substance solution.

5. Sample Determination

10 μL of the sample solution was precisely pipetted, injected into the liquid chromatography and determined.

The obtained fingerprints are as shown in FIG. 1-FIG. 4. The peaks of the fingerprints were well separated under the mobile phase elution gradient 1, while the peaks of the fingerprints were difficult to separate under the mobile phase elution gradient 2 and 3.

Experiment 2 Fingerprint Comparison

Instruments and equipment, reagents and materials, and chromatographic conditions (mobile phase elution gradient 1) were the same with experiment 1.

Sample Preparation:

AB-8-1 eluent, AB-8-2 eluent and AB-8-3 eluent were prepared according to embodiment 1, and D101-1 eluent, D101-2 eluent and D101-3 eluent were prepared according to the comparative example 1. After concentration, the eluents were diluted to 20 mL with methanol solution with volume fraction of 50%, cooled to room temperature, shaken well, and filtered respectively to obtain the sample solutions.

10 μL of each sample solution was precisely pipetted and injected into the liquid chromatograph respectively for determination, and the results were shown in FIG. 5-FIG. 10. After AB-8 was eluted by 40% ethanol solution, the content of chlorogenic acid increased significantly. And each characteristic peak was obviously different from Kudingcha extract A prepared in embodiment 1, indicating that macroporous resin AB-8 could enrich chlorogenic acid in Kudingcha after elution with 40% ethanol solution, and the enrichment effect was significant. However, D101 resin column eluted with 40% ethanol solution and 80% ethanol solution had little effect on the Kudingcha extract.

Experiment 3 Determination of Chlorogenic Acid Content

1. Instruments and Equipment

High performance liquid chromatograph: Agilent Technologies 1260 Infinity II; Electronic balance: one-100000th analytical balance (Mettler Toledo MS105DU).

2. Reagents and Materials

Methanol (Fisher Chemical™, chromatographically pure), phosphoric acid (analytically pure), water (distilled water); chlorogenic acid (Shanghai Yuanye Biotechnology Co., Ltd, 5 mg); microporous filter membrane (BOJIN, nylon 0.22 μm), syringe (Jiangxi Qingshantang medical device, 1 mL).

3. Chromatographic Conditions

Shimadzu Shim-pack VP-ODS-C18 (4.6×250 mm, 5 μm) with octadecyl silane bonded silica gel as filler; acetonitrile-0.4% phosphoric acid solution (13:87) was used as mobile phase; and the detection wavelength was 327 nm. The number of theoretical plates should not be less than 2000 according to the calculation of chlorogenic acid peak.

4. Preparation of Reference Solution

The chlorogenic acid reference substance was taken, weighed accurately, put into a brown measuring bottle, and added with methanol aqueous solution with volume fraction of 50% to prepare the reference solution.

5. Preparation of Test Sample Solution

The Kudingcha extract A, AB-8-2 Kudingcha extract, AB-8-3 Kudingcha extract prepared in embodiment 1, and D101-2 Kudingcha extract and D101-3 Kudingcha extract prepared in comparative example 1 were taken as samples.

0.1 g of each sample was weighed accurately into a 25 ml conical flask, 25 mL of methanol aqueous solution with volume fraction of 50% was accurately added and weighed to obtain a solution. After weighing, the solution was sonicated at 35 °C for 60 min, taken out and cooled to room temperature. Then the solution that has been made up of the weight loss by methanol aqueous solution with volume fraction of 50% was shaken well and filtered with 0.22 μm filter membrane to obtain the test sample solution.

6. Determination

10 μL of the reference solution and 10 μL of the test sample solution were precisely pipetted and injected into the liquid chromatograph for determination respectively.

Figure 11:
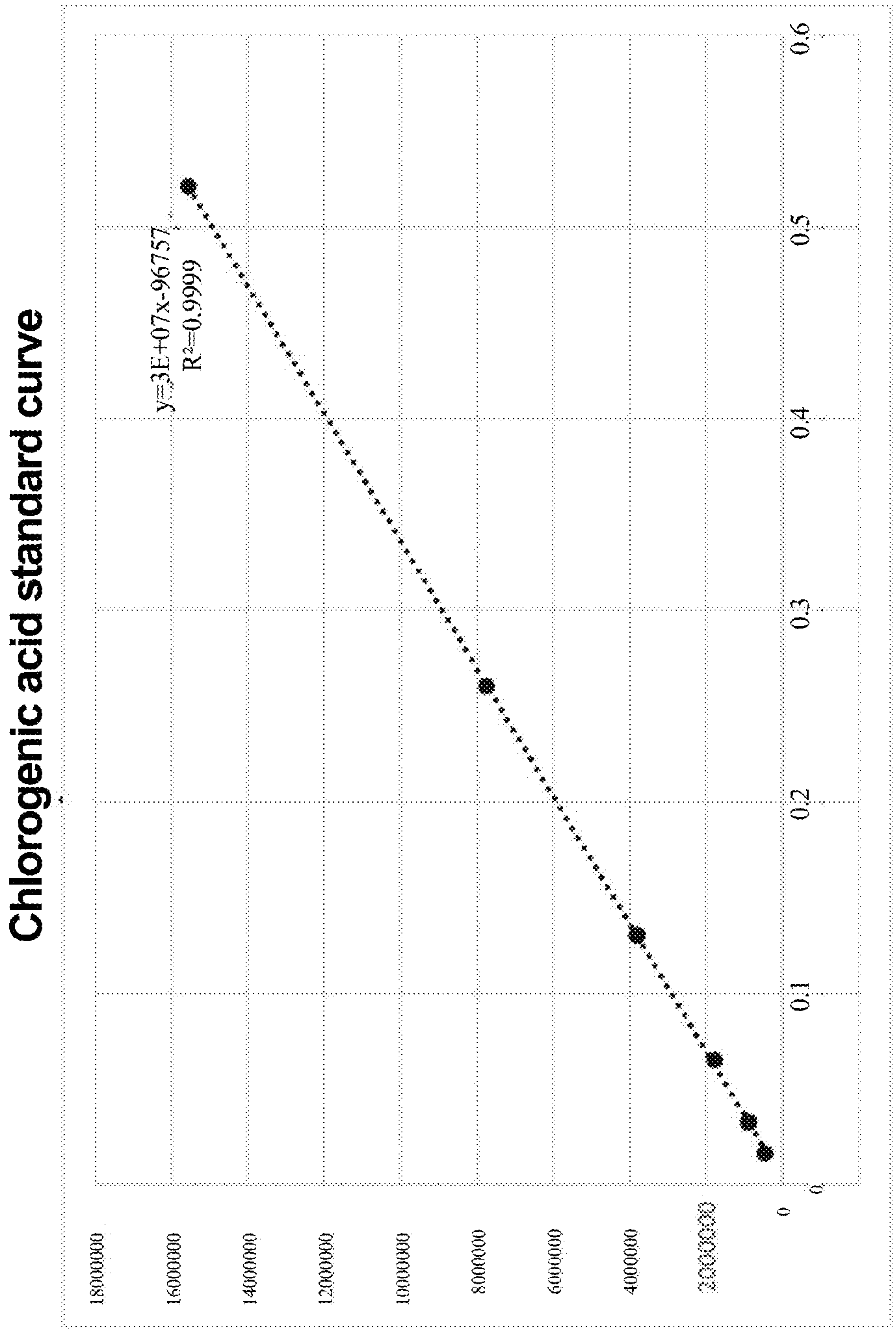
FIG. 11 shows a chlorogenic acid standard curve.

The standard curve plotted against the reference substance was $y=3E+07x-96757$, $r^2=0.9999$ (FIG. 11, 5 mg of chlorogenic acid reference substance was added with methanol water with volume fraction of 50% to a constant volume of 10 mL, and a six-point standard curve was prepared by double dilution method). The concentration of chlorogenic acid was calculated through the standard curve and the test sample determination results, and then the content of chlorogenic acid in each sample was calculated, as shown in Table 4.

TABLE 4

Content of chlorogenic acid in each sample

| | D101 | | AB-8 | |
|---|---|---|---|---|
| Kudingcha extract A | D101-2 Kudingcha extract | D101-3 Kudingcha extract | AB-8-2 Kudingcha extract | AB-8-3 Kudingcha extract |
| 4.98% | 0.01% | 0.02% | 16.68% | 0.30% |

Chlorogenic acid has a wide range of biological activities, with such diverse effects as scavenging free radicals and exciting the central nervous system, as an efficacy component of Kudingcha extract as well as a characteristic component of quality control. As known from the above data in Table 4, the content of the chlorogenic acid of the Kudingcha extract was 4.98% after the enzymolysis and water extraction process, and the content of chlorogenic acid in the AB-8-2 Kudingcha extract eluted and purified by the 40% ethanol elution and the AB-8 macroporous resin column was 16.68%, which increased by 335%. While the content in the AB-8-3 Kudingcha extract eluted and purified by the 80% ethanol elution was 0.30%, which was already quite small and negligible. It was demonstrated that most of the chlorogenic acid in the Kudingcha extract A was purified after 40% ethanol elution and purification with AB-8 macroporous resin column. For D101-2 Kudingcha extract and D101-3 Kudingcha extract after purification by D101 macroporous resin, the content of chlorogenic acid was minimal, which indicated that this resin column was not suitable for the purification and enrichment of active ingredients in Kudingcha extract A.

Experiment 4: Efficacy Experiment

1. Instruments and Consumables:

Swimming box (Shanghai Xinruan Information Technology Co., Ltd.), soda lime (Shanghai Wusi Chemical Reagent Co., Ltd., batch number: 20200713), white Vaseline (Shandong Lierkang Medical Technology Co., Ltd., batch number: 200701), electronic balance (Sartorius Group, Germany), mouse gavage device (Jinan Yiyan Technology Development Co., Ltd.).

2. Test Sample:

The test samples were Kudingcha extract A prepared in embodiment 1 and AB-8-4 Kudingcha extract prepared in embodiment 2.

Positive drug: black classic concentrate of Monster Claw, with the concentration ratio of 330 mL to 180 mL.

3. Animal:

80 SPF male KM mice with a body mass of 20±2 g were provided by Beijing Vital River Laboratory Animal Technology Co., Ltd. with the license number of SCXK (Beijing) 20210006.

4. Feeding Conditions, Grouping and Administration:

Five mice per cage were housed in a light, temperature and humidity controlled room with free access to food and water: temperature 21±2 °C, humidity 50±10%, 12 h/12 h light and dark cycle (lights on at 20:00, lights off at 8:00). All animal experiments were conducted in accordance with the guidelines for the welfare and use of experimental animals issued by NIH.

The mice were acclimatized to enter the experiment one week after arrival. There were 20 animals in each group, which were divided into 3 groups according to the randomized block design method, as shown in Table 5.

TABLE 5

Experimental grouping

| Group | Dosing in mice g/kg |
|---|---|
| Normal control | / |
| Positive control | 30 mL/kg |
| Kudingcha extract A group | 0.0835 |
| AB-8-4 Kudingcha extract group | 0.0835 |

The Kudingcha extract A group and AB-8-4 Kudingcha extract group were all administered 0.0835 g/kg dissolved in pure water. The normal control group was gavaged with the same volume of normal saline. Mice were gavaged every morning at fixed time (9:00) with a gavage volume of 0.1 ml·10 $g^{-1}$, and the administration lasted for 28 days.

5. Weight-Bearing Swimming Experiment

During the period of drug administration, a 5-min non-weight-bearing swimming adaptive training was performed every 3 days. Ten mice from each group were randomly selected, and after 1 h of gavage on day 28, a lead wire with 7% of the mouse body mass was tied to the caudal root of the mouse to create the weight-bearing status of the mouse, and the mice were immediately placed into a 50 cm×40 cm×40 cm tank to swim. The water depth was controlled not to be less than 30 cm and the water temperature was 25±1 °C. And the time from the start of swimming to the time when the mice could not come out of the water for 10 seconds after sinking was recorded with a time stopwatch as the time for the mice to be exhausted from swimming, that is, exhaustion time. The first sinking time and exhaustion time were recorded.

Experimental data were presented as $\bar{x}$+SE, and statistical analysis was performed by GraphPad Prism™ 8.02 software (Statistical Analysis System, GraphPad software, Inc., San Diego, California, USA). Kolmogorov-Smirnov test and Levene test were performed before parametric tests for all groups of data. An unpaired T-test (one tailed) was applied for pairwise comparisons between groups for all test parameters, and the testing level was set at $p<0.05$.

As shown in Table 6, compared with the normal control group in the weight-bearing swimming experiment, Kudingcha extract A could significantly prolong the first sinking time of the weight-bearing swimming of mice, and Kudingcha extract A, AB-8-4 Kudingcha extract all significantly increased the exhaustion time of the weight-bearing swimming of mice.

TABLE 6

Results of weight-bearing swimming experiment of mice ($\bar{x}$ ± SE)

| Group | Dose (g/kg) | Quantity | First sinking time (s) | Exhaustion time (s) |
|---|---|---|---|---|
| Normal control | / | 10 | 29.73 ± 8.380 | 71.32 ± 11.08 |
| Positive control | 30 ml/kg | 10 | 53.00 ± 8.155* | 147.4 ± 24.16** |
| Kudingcha extract A group | 0.0835 | 10 | 41.28 ± 6.639 | 123.6 ± 20.92* |

TABLE 6-continued

Results of weight-bearing swimming experiment of mice ($\bar{x}$ ± SE)

| Group | Dose (g/kg) | Quantity | First sinking time (s) | Exhaustion time (s) |
|---|---|---|---|---|
| AB-8-4 Kudingcha extract group | 0.0835 | 10 | 55.52 ± 9.119* | 168.9 ± 50.51* |

(*compared to the normal control group p < 0.05, ** compared to the normal control group p < 0.01)

(*compared to the normal control group p<0.05, ** compared to the normal control group p<0.01)

6. Normobaric Hypoxia Tolerance Experiment

At rest for 1 day after the last weight-bearing swimming experiment, 1 h after gavage on the 29th day, 10 mice in each group were placed into 250 ml abrasive mouth bottles soaked with 5 g of soda lime respectively, 1 in each bottle, and the bottles were sealed with stoppers pre coated with Vaseline so that they did not leak air, and the timing started immediately. The time of death of the mice due to hypoxia was immediately recorded, with the respiratory arrest as an indicator. And hypoxia tolerance time calculation was performed according to the following criteria: $T=(T1-T0)/(V0-W0/0.94)\times100$ (where T1 was the time of mouse death, T0 was the time at which closure starts, V0 was the effective bottle volume, W0 was the mouse weight, and 0.94 was the mouse density determined by drainage method).

Experimental data were presented as $\bar{x}$±SE, and statistical analysis was performed by GraphPad Prism™ 8.02 software (Statistical Analysis System, GraphPad software, Inc., San Diego, California, USA). Kolmogorov-Smirnov test and Levene test were performed before parametric tests for all groups of data. An unpaired T-test (one tailed) was applied for pairwise comparisons between groups for all test parameters, and the testing level was set at p<0.05.

As shown in Table 7, compared with the normal control group, both of the Kudingcha extract A and AB-8-4 Kudingcha extract could significantly prolong the hypoxia tolerance time of mice.

TABLE 7

Results of normobaric hypoxia tolerance experiment of mice ($\bar{x}$ ± SE)

| Group | Dose (g/kg) | Quantity | Hypoxia tolerance time (s) |
|---|---|---|---|
| Normal control | / | 10 | 1026 ± 45.38 |
| Positive control | 30 mL/kg | 10 | 1183 ± 57.21* |
| Kudingcha extract A group | 0.0835 | 10 | 1185 ± 35.12** |
| AB-8-4 Kudingcha extract group | 0.0835 | 10 | 1270 ± 58.72** |

(*compared to the normal control group p < 0.05, ** compared to the normal control group p < 0.01)

7. Blood Sample Detection Experiments 7.1 Measurement of Blood Lactate and LDH and Tissue Harvest (Rest of the Mice)

During the period of drug administration, a 5-min non-weight-bearing swimming adaptive training was performed every 3 days. The remaining 10 mice in each group swam in a 50 cm×40 cm×40 cm tank after 1 h of gavage on day 28. The water depth was controlled not to be less than 30 cm and the water temperature was 25±1 °C. And after 1 h of weight-bearing swimming (preexperiments determined the accurate wire weight occupancy that would enable mice to swim for slightly greater than 1 h), the mice were removed, and after 30 min, the mice were anesthetized with isoflurane. After the animals entered deep anesthesia as detected by the eyelid reflex, blood sampling from the abdominal aorta was performed in all animals. After the obtained blood of the animals stood for 30 min at room temperature, the supernatant was obtained by centrifugation at 3500 rpm/15 min and stored in a −80 °C freezer for detection.

Content Detection of Muscle Lactate, Muscle ATP, Muscle Glycogen, Liver Glycogen, SOD and MDA Mouse muscle lactate, muscle glycogen, liver glycogen content, SOD and MDA were detected using ELISA kits, and the AMP/ATP ratio was calculated. The frozen mouse quadriceps muscle tissues and livers were removed and thawed (−20 °C, 4 °C). The tissues were rinsed with pre-chilled PBS (0.01 M, pH=7.4) to remove residual blood, and the tissues were sheared. Four or five sterile steel beads were placed into the sheared tissue and the corresponding volume of PBS (with a weight-to-volume ratio of 1:9, 1 g of tissue sample corresponds to 9 mL of PBS, and records were made). After homogenization using a tissue homogenizer, the supernatant was obtained by centrifugation (13000 rpm/10 min) after freezing-thawing twice (−20 °C, 4 °C). And the detection was performed according to the relevant kit instructions. Within 5 min of reaction termination, the concentration values of each standard on the test kit were entered, and the optical density (OD) values of each group were measured sequentially with a microplate reader at the specified value wavelengths. After the standard curve was obtained, the sample OD values were substituted within the resulting regression equation to obtain concentrations of each sample. If the detected samples were diluted, the final sample concentration needed to be multiplied by the dilution factor required.

7.3 Statistical Method

Experimental data were presented as $\bar{x}$±SE, and statistical analysis was performed by GraphPad Prism™ 8.02 software (Statistical Analysis System, GraphPad software, Inc., San Diego, California, USA). Kolmogorov-Smirnov test and Levene test were performed before parametric tests for all groups of data. An unpaired T-test (one tailed) was applied for pairwise comparisons between groups for all test parameters, and the testing level was set at p<0.05.

7.4 Blood Lactate, Lactate Dehydrogenase (LDH) Content

TABLE 8

Results of mouse blood lactate and LDH experiment ($\bar{x}$ ± SE)

| Group | Dose (g/kg) | Quantity | Blood lactate (mmol/L) | LDH (U/L) |
|---|---|---|---|---|
| Normal control | / | 9 | 4.800 ± 0.3370 | 2915 ± 124.6 |
| Positive control | 30 ml/kg | 9 | 4.034 ± 0.1846* | 3308 ± 165.6* |
| Kudingcha extract A group | 0.0835 | 9 | 3.999 ± 0.2399* | 3322 ± 190.7* |
| AB-8-4 Kudingcha extract group | 0.0835 | 10 | 3.277 ± 0.2759** | 3319 ± 245.1 |

*compared to the normal control group $p < 0.05$, **compared to the normal control group $p < 0.01$

TABLE 9

Results of mouse blood lactate and LDH experiment ($\bar{x}$ ± SE)

| Group | Dose (g/kg) | Quantity | Blood lactate (mmol/L) | LDH (U/L) |
|---|---|---|---|---|
| Normal control | / | 9 | 4.800 ± 0.3370 | 2915 ± 124.6 |
| Positive control | 30 ml/kg | 9 | 4.034 ± 0.1846 | 3308 ± 165.6 |
| Kudingcha extract A group | 0.0835 | 9 | 3.999 ± 0.2399 | 3322 ± 190.7 |
| AB-8-4 Kudingcha extract group | 0.0835 | 9 | 3.277 ± 0.2759# | 3319 ± 245.1 |

#compared to the positive control group $p < 0.05$

TABLE 10

Results of mouse blood lactate and LDH experiment ($\bar{x}$ ± SE)

| Group | Dose (g/kg) | Quantity | Blood lactate (mmol/L) | LDH (U/L) |
|---|---|---|---|---|
| Normal control | / | 9 | 4.800 ± 0.3370 | 2915 ± 124.6 |
| Positive control | 30 ml/kg | 9 | 4.034 ± 0.1846 | 3308 ± 165.6 |
| Kudingcha extract A group | 0.0835 | 9 | 3.999 ± 0.2399 | 3322 ± 190.7 |
| AB-8-4 Kudingcha extract group | 0.0835 | 9 | 3.277 ± 0.2759$ | 3319 ± 245.1 |

$compared with Kudingcha water extract A group, $p < 0.05$

Compared with the normal control group, the gavage of positive drug (black classic of Monster Claw), the Kudingcha extract A group and AB-8-4 Kudingcha extract group all significantly reduced the blood lactic acid content of mice. The gavage of positive drug (black classic of Monster Claw) and the Kudingcha extract A group could significantly increase the blood lactate dehydrogenase levels in mice. Compared with the positive control group, the gavage of AB-8-4 Kudingcha extract group more significantly reduced the blood lactate content of mice. There were significant differences between the Kudingcha extract A group and the AB-8-4 Kudingcha extract group.

7.5 Content of Muscle Lactate, Muscle ATP, Muscle Glycogen, Liver Glycogen, Superoxide Dismutase (SOD) and Malondialdehyde (MDA)

TABLE 11

Experimental result of muscle lactate, muscle ATP, muscle glycogen, liver glycogen, SOD and MDA of mice ($\bar{x}$ ± SE)

| Group | Dose (g/kg) | Quantity | Muscle lactate (mmol/L) | Muscle ATP (U/mgprot) |
|---|---|---|---|---|
| Normal control group | / | 9 | 3.778 ± 0.2974 | 1.390 ± 0.1572 |
| Positive control group | 30 ml/kg | 10 | 3.712 ± 0.1900* | 1.858 ± 0.06741** |
| Kudingcha extract A group | 0.0835 | 10 | 2.849 ± 0.2070* | 1.801 ± 0.1161* |
| AB-8-□ Kudingcha extract group | 0.0835 | 9 | 2.611 ± 0.1500** | 1.775 ± 0.1398* |

TABLE 11-continued

Experimental result of muscle lactate, muscle ATP, muscle glycogen, liver glycogen, SOD and MDA of mice ($\bar{x}$ ± SE)

| Group | Muscle glycogen (mg/g) | Liver glycogen (mg/g) | SOD (U/mgprot) | MDA (nmol/mL) |
|---|---|---|---|---|
| Normal control group | 0.7680 ± 0.03913 | 3.805 ± 0.5917 | 56.99 ± 0.7634 | 19.52 ± 3.321 |
| Positive control group | 0.8691 ± 0.07335 | 6.033 ± 0.7460* | 62.17 ± 1.243** | 14.18 ± 2.912 |
| Kudingcha extract A group | 1.072 ± 0.06745** | 6.066 ± 1.121 | 60.29 ± 1.408* | 8.302 ± 2.123** |
| AB-8-□ Kudingcha extract group | 0.9203 ± 0.08213* | 7.083 ± 1.179* | 54.76 ± 1.692 | 17.17 ± 2.298 |

*compared with normal control group p < 0.05,
**compared with normal control group p < 0.01,
**compared with normal control group p < 0.001

TABLE 12

Experimental result of muscle lactate, muscle ATP, muscle glycogen, liver glycogen, SOD and MDA of mice ($\bar{x}$ ± SE)

| Group | Dose (g/kg) | Quantity | Muscle lactate (mmol/L) | Muscle ATP (U/mgprot) |
|---|---|---|---|---|
| Normal control group | / | 9 | 3.778 ± 0.2974 | 1.390 ± 0.1572 |
| Positive control group | 30 ml/kg | 10 | 3.712 ± 0.1900 | 1.858 ± 0.06741 |
| Kudingcha extract A group | 0.0835 | 10 | 2.849 ± 0.2070 | 1.801 ± 0.1161 |
| AB-8-□ Kudingcha extract group | 0.0835 | 9 | 2.611 ± 0.1500 | 1.775 ± 0.1398 |

| Group | Muscle glycogen (mg/g) | Liver glycogen (mg/g) | SOD (U/mgprot) | MDA (nmol/mL) |
|---|---|---|---|---|
| Normal control group | 0.7680 ± 0.03913 | 3.805 ± 0.5917 | 56.99 ± 0.7634 | 19.52 ± 3.321 |
| Positive control group | 0.8691 ± 0.07335 | 6.033 ± 0.7460 | 62.17 ± 1.243 | 14.18 ± 2.912 |
| Kudingcha extract A group | 1.072 ± 0.06745# | 6.066 ± 1.121 | 60.29 ± 1.408 | 8.302 ± 2.123 |
| AB-8-□ Kudingcha extract group | 0.9203 ± 0.08213 | 7.083 ± 1.179 | 54.76 ± 1.692## | 17.17 ± 2.298 |

#compared with positive control group p < 0.05,
compared with positive control group p < 0.01,
compared with positive control group p < 0.001

TABLE 13

Experimental result of muscle lactate, muscle ATP, muscle glycogen, liver glycogen, SOD and MDA of mice ( $\bar{x}$ ± SE)

| Group | Dose (g/kg) | Quantity | Muscle lactate (mmol/L) | Muscle ATP (U/mgprot) |
|---|---|---|---|---|
| Normal control group | / | 9 | 3.778 ± 0.2974 | 1.390 ± 0.1572 |
| Positive control group | 30 ml/kg | 10 | 3.712 ± 0.1900 | 1.858 ± 0.06741 |
| Kudingcha extract A group | 0.083 | 10 | 2.849 ± 0.2070 | 1.801 ± 0.1161 |

TABLE 13-continued

Experimental result of muscle lactate, muscle ATP, muscle glycogen, liver glycogen, SOD and MDA of mice ( $\overline{x}$ ± SE)

| | | | | |
|---|---|---|---|---|
| AB-8-□ Kudingcha extract group | 0.021 | 9 | 2.611 ± 0.1500 | 1.775 ± 0.1398 |

| Group | Muscle glycogen (mg/g) | Liver glycogen (mg/g) | SOD (U/mgprot) | MDA (nmol/mL) |
|---|---|---|---|---|
| Normal control group | 0.7680 ± 0.03913 | 3.805 ± 0.5917 | 56.99 ± 0.7634 | 19.52 ± 3.321 |
| Positive control group | 0.8691 ± 0.07335 | 6.033 ± 0.7460 | 62.17 ± 1.243 | 14.18 ± 2.912 |
| Kudingcha extract A group | 1.072 ± 0.06745 | 6.066 ± 1.121 | 60.29 ± 1.408 | 8.302 ± 2.123 |
| AB-8-□ Kudingcha extract group | 0.9203 ± 0.08213 | 7.083 ± 1.179 | 54.76 ± 1.692$ | 17.17 ± 2.298$$ |

$compared with Kudingcha extract A group p < 0.05,
$$compared with Kudingcha extract A group p < 0.01

Compared with the normal control group, the gavage of positive drug (black classic of Monster Claw), Kudingcha extract A group and AB-8-4 Kudingcha extract group could significantly reduce the muscle lactic acid content of mice. The gavage of positive drug (black classic of Monster Claw), Kudingcha extract A group and AB-8-4 Kudingcha extract group could significantly increase the muscle ATP content of mice. The gavage of Kudingcha extract A group and AB-8-4 Kudingcha extract group Kudingcha water extract significantly increased the muscle glycogen content of mice. The gavage of positive drug (black classic of Monster Claw) and AB-8-4 Kudingcha extract group could significantly elevate the liver glycogen content of mice. The gavage of positive drug (black classic of Monster Claw) and Kudingcha extract A group could significantly elevated the level of SOD in mice. The gavage of Kudingcha extract A group could significantly decreased the MDA content in mice.

Compared with the positive control group, the gavage of Kudingcha extract A group more significantly elevated the muscle glycogen content of mice, and AB-8-4 Kudingcha extract group more significantly reduced the muscle SOD content of mice.

In the aspect of muscle lactic acid content and SOD, there was a significant difference between the AB-8-4 Kudingcha extract group and the Kudingcha extract A group. In the aspect of MDA, there was a significant difference between the AB-8-4 Kudingcha extract group and the Kudingcha extract A group.

From the comprehensive analysis of the above pharmacodynamic experimental results, it is known that the Kudingcha through enzymolysis and water extraction process (Kuidngcha extract A group in embodiment 1), and Kudingcha through macroporous resin purification process after enzymolysis and water extraction (AB-8-4 Kudingcha extract in embodiment 2), had the effect of prolonging the exhaustion time of weight-bearing swimming of mice compared with the normal control group, in which the effect of the Kudingcha through macroporous resin purification process after enzymolysis and water extraction was more significant, and it was also possible to prolong the first sinking time of weight-bearing swimming of mice.

In the detection of biochemical indexes, both Kudingcha extract through enzymolysis and water extraction process and Kudingcha extract through macroporous resin purification process after enzymolysis and water extraction process, had the effect of reducing blood lactate. The gavage of the extract through macroporous resin purification process after enzymolysis and water extraction more significantly reduced the blood lactate content in mice and showed significant differences from the normal control group, the positive control group, and the extract group through enzymolysis and water extraction process. It suggested that the improvement of lactic acid stacking of the body by the extract through macroporous resin purification process after enzymolysis and water extraction is significant. The extract through macroporous resin purification process after enzymolysis and water extraction significantly decreased the muscle lactic acid content, significantly increased the muscle ATP content, muscle glycogen content, liver glycogen content in mice, and showed significant differences in muscle lactic acid content, SOD and MDA aspects compared with that of the Kudingcha extract through only enzymolysis and water extraction. It suggested that the extract after macroporous resin purification process after enzymolysis and water extraction had an improved effect on the energy metabolism of muscle.

Through comprehensive analysis, it can be seen that the extract through macroporous resin purification process after enzymolysis and water extraction has a very good anti-fatigue effect, which is more significant than the extract without macroporous resin purification process.

Experiment 5 Bitter Taste Through Trial

1. Materials: disposable paper cups, marker pen, the Kudingcha extract A and AB-8-4 Kudingcha extract prepared in embodiment 1.
2. Experimenters: 12 company personnel (Qingdao Chenlan Biotechnology Co., Ltd)
3. Experimental procedure:

4 g of the Kudingcha extract A and 4 g of AB-8-4 Kudingcha extract prepared in embodiment 1 were taken, dissolved in 2 L of purified water, and poured into 24 disposable paper cups after full dissolution, respectively. The bottoms of the cups were marked by a pencil (which could not be seen by the tasters), where the cups corresponding to Kudingcha extract A were marked A, and the cups corresponding to AB-8-4 Kudingcha extract were marked B. The cup sides were randomly numbered 1-48, and the cups marked A were placed in trays numbered 1, 3, and the cups marked B were placed in trays numbered 2, 4.

Twelve tasters randomly took the cups from trays 1, 2, 3, and 4, and recorded them after tasting and scoring. The scoring was anonymous with the following scoring criteria:

0 points - - - no bitter;

1 point - - - a little bitter;

2 points - - - bitter;

3 points - - - very bitter.

The experimental results are shown in Tables 14 and Table 15.

TABLE 14

Scoring records of bitter taste

Scoring records of bitter taste

| Cup number | 0 | 1 | 2 | 3 | Actual number |
|---|---|---|---|---|---|
| 1 | | | √ | | A |
| 2 | | | | √ | A |
| 3 | | | | √ | A |
| 4 | | | √ | | B |
| 5 | | | √ | | B |
| 6 | | | | √ | A |
| 7 | | | | √ | A |
| 8 | | | √ | | B |
| 9 | | | | √ | A |
| 10 | | | | √ | A |
| 11 | | √ | | | B |
| 12 | | | | √ | A |
| 13 | | | | √ | B |
| 14 | | | √ | | A |
| 15 | | √ | | | B |
| 16 | √ | | | | B |
| 17 | | | √ | | B |
| 18 | | √ | | | B |
| 19 | | | | √ | A |
| 20 | | √ | | | B |
| 21 | | | | √ | A |
| 22 | | | | √ | A |
| 23 | | | √ | | B |
| 24 | | | | √ | A |
| 25 | | | | √ | B |
| 26 | | | √ | | B |
| 27 | | | √ | | B |
| 28 | | | | √ | A |
| 29 | | | √ | | B |
| 30 | | | √ | | B |
| 31 | | | √ | | B |
| 32 | | √ | | | B |
| 33 | | | | √ | A |
| 34 | | | √ | | B |
| 35 | | | | √ | A |
| 36 | | | | √ | B |
| 37 | | | | √ | A |
| 38 | | | | √ | A |
| 39 | | | | √ | A |
| 40 | | | | √ | A |
| 41 | | | √ | | A |
| 42 | | | √ | | A |
| 43 | | | | √ | A |
| 44 | | | √ | | A |
| 45 | | | √ | | B |
| 46 | | | √ | | B |
| 47 | | √ | | | B |
| 48 | | √ | | | B |

TABLE 15

Scoring statistical results

| Group | A | B |
|---|---|---|
| 1 | 2 | 2 |
| 2 | 3 | 2 |
| 3 | 3 | 2 |
| 4 | 3 | 1 |
| 5 | 3 | 0 |
| 6 | 3 | 1 |
| 7 | 3 | 3 |
| 8 | 3 | 2 |
| 9 | 2 | 1 |
| 10 | 3 | 1 |
| 11 | 3 | 2 |
| 12 | 3 | 3 |
| 13 | 3 | 2 |
| 14 | 3 | 2 |
| 15 | 3 | 2 |
| 16 | 3 | 2 |
| 17 | 3 | 2 |
| 18 | 3 | 1 |
| 19 | 3 | 2 |
| 20 | 3 | 3 |
| 21 | 2 | 2 |
| 22 | 2 | 2 |
| 23 | 3 | 1 |
| 24 | 2 | 1 |
| Average value | 2.79 | 1.75 |
| Significance | T = 6.0327 P < 0.01 | |

The results showed that the Kudingcha extract through macroporous resin purification process had significant improvement on taste, better debittering effect, and the taste was between a little bitter and bitter, while the Kudingcha extract without macroporous resin purification process had a stronger bitter taste and poor palatability.

The above description of the disclosed embodiments enables the skilled in the art to achieve or use the disclosure. Multiple modifications to these embodiments will be apparent to those skilled in the art, and the general principles defined herein may be achieved in other embodiments without departing from the spirit or scope of the disclosure. The present disclosure will therefore not be restricted to these embodiments shown herein, but rather to comply with the broadest scope consistent with the principles and novel features disclosed herein.

What is claimed is:

1. A preparation method of a debittering Kudingcha extract with anti-fatigue effect, comprising:

S1 crushing Kudingcha, adding water and an enzyme preparation, and carrying out enzymolysis;

S2 adding water after the enzymolysis, carrying out water extraction to obtain extraction solutions, then combining the extraction solutions, and carrying out filtering, concentrating and drying to obtain extract powder;

S3 preparing the extract powder into a solution by adding water, and then carrying out purification and enrichment with macroporous resin column:

loading sample, rinsing the macroporous resin column with pure water, discarding the water eluent, and carrying out elution with an ethanol solution with volume fraction of 30-80%, and collecting the ethanol eluent;

wherein the macroporous resin is crosslinked polystyrene adsorption resin; and

S4 drying the ethanol eluent to obtain the debittering Kudingcha extract, wherein in step (1), a mass ratio of Kudingcha to water is 1:2-1:3;

the enzyme preparation is a composite enzyme preparation compounded by cellulase, pectinase and plant hydrolysis composite enzyme in a mass ratio of 2:1:1;

the enzymolysis is carried out under following conditions: an amount of the enzyme preparation is 0.2%-0.3% of the dry sample of Kudingcha, a time of the enzymolysis is 40-60 min, a temperature is 45-50 °C, and a pH value is 4.5-5.5.

2. The preparation method of claim 1, wherein in step (2), a mass ratio of the Kudingcha to water is 1:6-1:12;

a number of times of the extraction are 1-3, and each time is 1-3 h;

the filtering is carried out using an 80-100 mesh sieve; and a specific gravity of a concentrated extract obtained by the concentrating is 1.01-1.08.

3. The preparation method of claim 1, wherein in step (3), a sample loading concentration is 3-10 mg/mL, and a sample loading volume is 1-3 times of the column volume;

a volume of pure water rinsing is 3-5 times of the column volume;

an elution volume of the ethanol solution is 2-4 times of the column volume;

a flow rate of the sample loading, pure water rinsing and ethanol solution elution is 1.5 times of column volume/h;

a ratio of column height to diameter of the macroporous resin column is 1:6-1:8; and the crosslinked polystyrene adsorption resin is AB-8.

4. The preparation method of claim 1, wherein in step (1) or (4), the drying is spray drying or hypobaric drying;

the spray drying parameters are: inlet air temperature 120 °C, outlet air temperature 90 °C, centrifugal frequency 300 Hz, feed pump 17 rpm, induced air frequency 50 Hz.

* * * * *